(12) United States Patent
Turner et al.

(10) Patent No.: US 8,079,518 B2
(45) Date of Patent: Dec. 20, 2011

(54) DEVICES AND METHODS FOR IMPLANT TRACKING

(75) Inventors: Robin L Turner, Memphis, TN (US); Thor M Hanna, Memphis, TN (US); Casey Doherty, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 228 days.

(21) Appl. No.: 12/512,274

(22) Filed: Jul. 30, 2009

(65) Prior Publication Data

US 2011/0023343 A1    Feb. 3, 2011

(51) Int. Cl.
G06F 19/00 (2006.01)
G06Q 30/00 (2006.01)
G06Q 90/00 (2006.01)

(52) U.S. Cl. .................................... 235/385; 235/375

(58) Field of Classification Search ............... 235/385, 235/375, 487; 600/29–32, 37
See application file for complete search history.

(56) References Cited

U.S. PATENT DOCUMENTS

| | | | |
|---|---|---|---|
| 4,154,342 A | 5/1979 | Wallace | |
| 4,501,363 A | 2/1985 | Isbey, Jr. | |
| 4,553,669 A | 11/1985 | Butterworth et al. | |
| 4,856,648 A | 8/1989 | Krueger | |
| 5,199,567 A | 4/1993 | Discko, Jr. | |
| 5,636,736 A | 6/1997 | Jacobs | |
| 5,759,028 A | 6/1998 | Bozman | |
| 5,762,192 A | 6/1998 | Jacobs | |
| 5,887,707 A | 3/1999 | Anascavage | |
| 5,934,460 A | 8/1999 | Schmid | |
| 5,967,305 A | 10/1999 | Blonder | |
| 6,328,746 B1 | 12/2001 | Gambale | |
| 6,373,786 B1 | 4/2002 | Kagan | |
| 6,375,956 B1 | 4/2002 | Hermelin | |
| 6,415,916 B1 | 7/2002 | Rini | |
| 7,048,120 B2 | 5/2006 | Pond | |
| 7,118,029 B2 | 10/2006 | Nycz et al. | |
| 7,213,767 B2 | 5/2007 | Tethrake et al. | |
| 7,256,699 B2 | 8/2007 | Tethrake et al. | |
| 7,268,684 B2 | 9/2007 | Tethrake et al. | |
| 7,338,282 B2 | 3/2008 | Corcoran | |
| 7,362,228 B2 | 4/2008 | Nycz et al. | |

(Continued)

FOREIGN PATENT DOCUMENTS

DE    202007004638    6/2007

(Continued)

OTHER PUBLICATIONS

Orthopedics This Week, vol. 4, Issue 4, p. 4, Feb. 5, 2008, "Radio Frequency Identification and Orthopedics."

(Continued)

*Primary Examiner* — Edwyn Labaze (57) ABSTRACT

A tag for tracking inventory levels and uses of an implant. The tag has a first component having a proximal portion and a distal portion and a second component having a proximal portion and distal portion. Additionally, the tag has an implant receiving cavity formed by the distal portion of the first component and the distal portion of the second component. Furthermore, the tag has a planar surface formed by the proximal portion of the first component and the proximal portion of the second component. The planar surface extending from the implant receiving cavity such that the planar surface is substantially transverse to a longitudinal axis of the implant received within the implant receiving cavity. In addition, the tag has a tamper evident locking mechanism configured for locking the first component to the second component. Additionally, at least a portion of the first and second components is radiopaque.

17 Claims, 7 Drawing Sheets

U.S. PATENT DOCUMENTS

| | | |
|---|---|---|
| 2002/0004660 A1 | 1/2002 | Henninges |
| 2004/0243207 A1 | 12/2004 | Olson |
| 2005/0033430 A1 | 2/2005 | Powers et al. |
| 2006/0144749 A1 | 7/2006 | Arnold |
| 2006/0145871 A1 | 7/2006 | Donati |
| 2006/0244652 A1 | 11/2006 | Tethrake et al. |
| 2006/0260958 A1 | 11/2006 | Brunner |
| 2007/0001839 A1 | 1/2007 | Cambre et al. |
| 2007/0095689 A1 | 5/2007 | Pratt et al. |
| 2007/0125392 A1 | 6/2007 | Olson et al. |
| 2007/0144926 A1 | 6/2007 | Bettenhausen et al. |
| 2007/0159337 A1 | 7/2007 | Tethrake et al. |
| 2007/0188306 A1 | 8/2007 | Tethrake et al. |
| 2007/0205126 A1 | 9/2007 | Elsener |
| 2007/0239289 A1 | 10/2007 | Cambre et al. |
| 2007/0284428 A1 | 12/2007 | Cambre et al. |
| 2008/0048855 A1 | 2/2008 | Berger |
| 2008/0230421 A1 | 9/2008 | Pleil et al. |
| 2008/0230422 A1 | 9/2008 | Pleil et al. |
| 2008/0230423 A1 | 9/2008 | Loeffler et al. |
| 2009/0118831 A1 | 5/2009 | Trieu |
| 2009/0266890 A1 | 10/2009 | Bagozzi |

FOREIGN PATENT DOCUMENTS

| | | |
|---|---|---|
| EP | 1842505 | 10/2007 |
| JP | 2008052013 | 3/2008 |
| KR | 1020060102826 | 9/2006 |
| WO | 2006124188 | 11/2006 |

OTHER PUBLICATIONS

International Search Report in realted Application No. PCT/US2009041760, mailed Aug. 11, 2009.

INternational Searching AUthority, IRS and Written Opinion, Jul. 31, 2009.

DEVICES AND METHODS FOR IMPLANT TRACKING

RELATED APPLICATIONS

This application is related to U.S. patent application Ser. No. 12/109,517, filed Apr. 25, 2008, to U.S. patent application Ser. No. 12/109,534, filed Apr. 25, 2008, and to U.S. patent application Ser. No. 12/109,539, filed Apr. 25, 2008, the disclosures of which are entirely incorporated herein by reference.

BACKGROUND

There is a strong and growing need to track non-sterile medical devices from their base materials and manufacture to their use, and throughout the intervening time. A non-sterile medical device is a medical device that is shipped from a manufacturer in a condition that is not adequately sterilized for implantation. By contrast, a sterile medical device is shipped from the manufacture in a condition adequately sterilized for implantation. Healthcare providers may prefer to receive non-sterile medical devices for various reasons. In that regard, because non-sterile devices can be sterilized onsite before a medical procedure, non-sterile medical devices having a longer shelf life than a corresponding sterile medical device. Furthermore, non-sterile medical devices are less expensive to package. Additionally, non-sterile medical devices typically can be more densely packaged into a common carrier than sterile devices.

However, difficulty arises in tracking non-sterile medical devices. For example, non-sterile medical devices are difficult to track because medical devices generally do not have adequate surface area for applying marks. Thus, in many instances, non-sterile medical devices are not tracked beyond their manufacturing facility, and may only be counted when reconciled for payment as one of many products that were not returned to a manufacturer for replenishment.

Accordingly, devices, systems and methods for tracking and tracing non-sterile medical devices are needed.

SUMMARY

Disclosed herein is a tag for tracking inventory levels and uses of an implant. The tag has a first component having a proximal portion and a distal portion and a second component having a proximal portion and distal portion. Additionally, the tag has an implant receiving cavity formed by the distal portion of the first component and the distal portion of the second component. Furthermore, the tag has a planar surface formed by the proximal portion of the first component and the proximal portion of the second component. The planar surface extending from the implant receiving cavity such that the planar surface is substantially transverse to a longitudinal axis of the implant received within the implant receiving cavity. Also, the planar surface includes indicia. In addition, the tag has a tamper evident locking mechanism configured for locking the first component to the second component. Additionally, at least a portion of the first and second components is radiopaque.

In another exemplary embodiment, a tag for tracking inventory levels and uses of an implant is disclosed. The tag having a first component with a first lobe and a second component with a second lobe forming an implant receiving cavity. The first lobe and the second lobe extending substantially perpendicular from a longitudinal axis of the implant received within the implant receiving cavity. The first and second lobes forming a planar surface having indicia. Also, the tag has a web flexibly connecting the first and second lobes such that the lobes are separable along a first plane that is substantially coplanar with the planar surface and along a second plane that is substantially transverse to the planar surface.

In another exemplary embodiment, a tag for tracking inventory levels and uses of an implant is disclosed. The tag having a first component and a second component forming an implant receiving cavity. Additionally, the tag having a first implant receiving aperture having a first longitudinal axis on the first component and an opposing second implant receiving aperture having a second longitudinal axis on the second component. The first and second implant receiving apertures sized and shaped for receiving the implant. Furthermore, in one aspect the tag has a hinge joining the first component to the second component and movable between an open position and a closed position. In addition, the tag has a stress relief structure defined on at least one of the first and second components. Also, in the open position the stress relief structure is in a relaxed condition and the first longitudinal axis is generally aligned with the second longitudinal axis and in the closed position the stress relief structure is in a flexed condition and the first longitudinal axis is generally skewed from the second longitudinal axis.

These and other aspects, forms, objects, features, and benefits of the present invention will become apparent from the following detailed drawings and description.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify the embodiments of this invention.

DETAILED DESCRIPTION

The present disclosure relates generally to the field of orthopedic surgery, and more particularly to devices, systems and methods for tracking and tracing medical devices through the use of removable tags. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein, are contemplated as would normally occur to one skilled in the art to which the disclosure relates.

Figure 1:
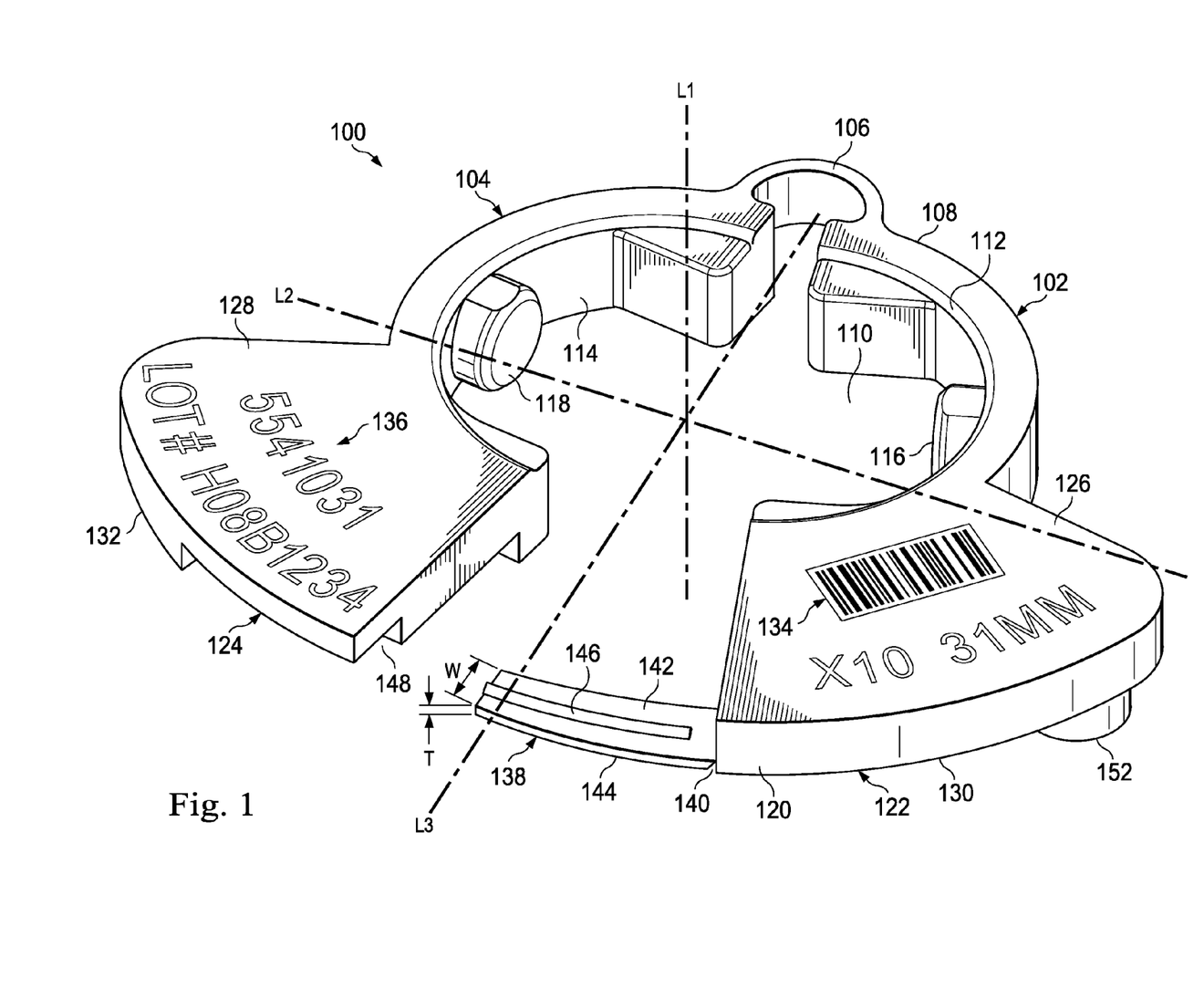
FIG. 1 is a perspective view of a tag for attachment to a medical device according to one embodiment of the present disclosure.

Referring first to FIG. 1, a perspective view of a tag 100 for attachment to a medical device is shown. Tag 100 is shown in an open or unlocked position ready to capture a medical device. Tag 100 has a first component 102 and second component 104. A hinge or web 106 flexibly connects the first component 102 and second component 104 to each other at a distal portion 108 of tag 100. Web 106 provides sufficient flexibility to allow the first and second components to move relative to each other along axes L1 (y-axis), L2 (x-axis), L3 (z-axis), and any intervening axis. In that regard, web 106 allows the first component 102 and second component 104 to remain attached to one another while the first and second components are positioned to capture a medical device therebetween.

Additionally, the distal portion of tag 100 defines an implant or medical device receiving cavity 110. In particular, portions 112 and 114 of the first and second components 102, 104 define the implant receiving cavity 110. As shown in FIG. 1, cavity 110 has a semi-rectangular shape to receive a medical device with the corresponding shape. However, it is contemplated that cavity 110 can be any shape in order to accommodate the medical device. For example, implant receiving cavity 110 can be circular, semi-circular, square, rectangular, trapezoidal, oblong, cylindrical, triangular, and any other shape necessary to receive the medical device within the cavity 110.

Furthermore, implant receiving cavity 110 is designed to allow at least a portion of a medical device to extend through cavity 110. In this manner, that tag 100 can be attached to a medical device at a plurality of locations. Additionally, it is contemplated that a portion of the medical device may extend from above and/or below cavity 110 while tag 100 is attached to the device.

Figure 2:
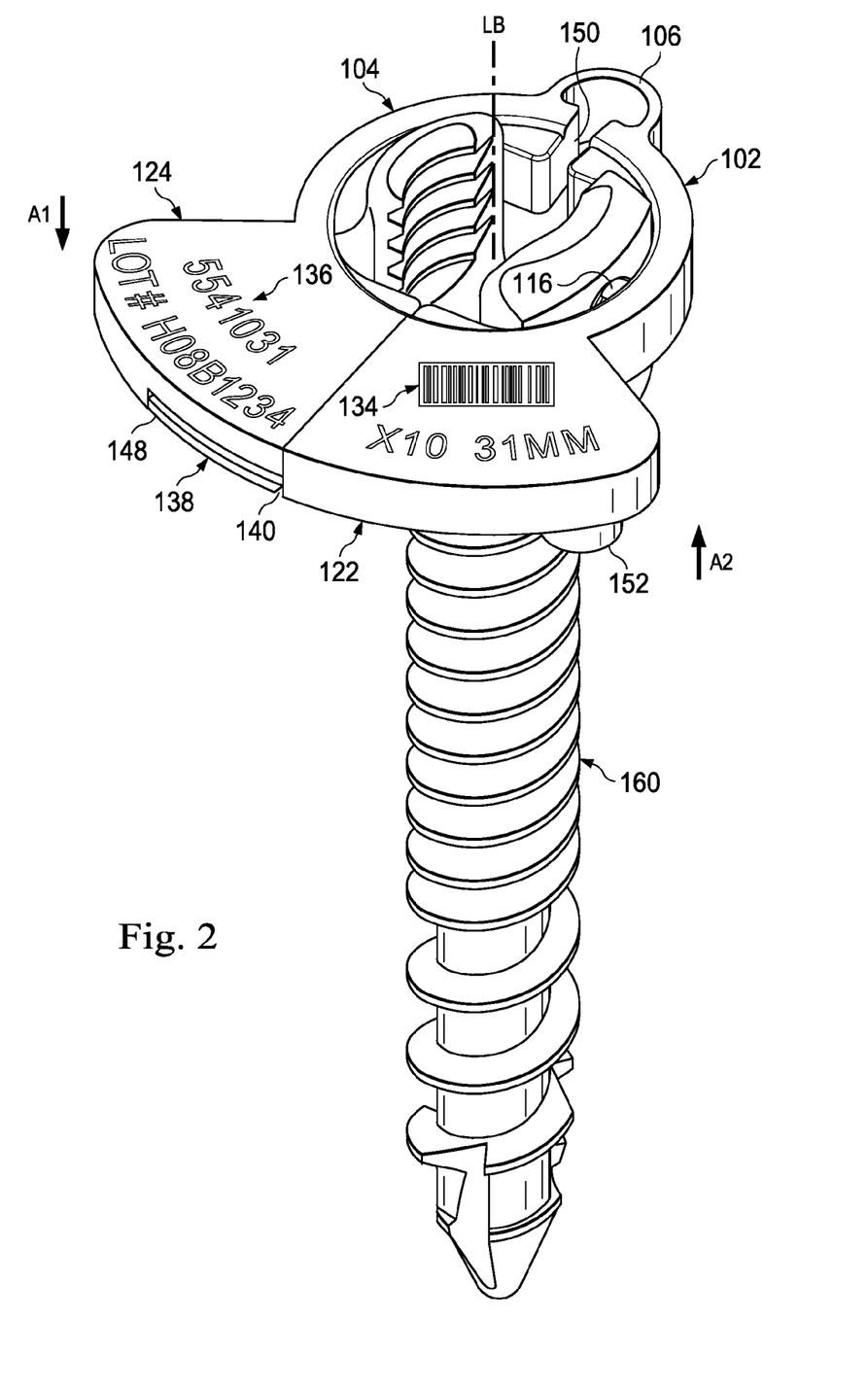
FIG. 2 is a perspective view of the tag of FIG. 1 locked onto a bone screw.

Implant receiving cavity 100 further includes projections 116 and 118. In that regard, projections 116 and 118 are designed to further secure a medical device within cavity 110 when tag 100 is in a closed or locked position as shown in FIG. 2. Projections 116 and 118 can be inserted into a corresponding aperture of a medical device to assist in securing tag 100 to the device. For example, as shown in FIG. 2, projections 116 and 118 are inserted into a head of bone screw 160 when tag 100 captures the screw. In this manner, tag 100 and bone screw 100 are in rotational alignment with one another because projections 116 and 118 received within the head portion of screw 160 prohibit tag 100 from rotating relative to bone screw 160.

Tag 100 further comprises a pair of lobes 122 and 124 that extend from implant receiving cavity 110 toward a proximal portion 120 of tag 100. As shown in FIG. 1, lobes 122 and 124 extend along a plane substantially transverse from axis L1 or, as shown in FIG. 2, substantially transverse from a longitudinal axis LB of bone screw 160. However, lobes 122 and 124 can extend at any angle with respect to axis L1 or L3.

Lobes 122 and 124 have upper planar surfaces 126 and 128 and opposing lower surfaces 130 and 132, respectively. Upper planar surfaces 126 and 128 provide a relatively large planar surface with respect to any portion of a medical device capture by tag 100. In that manner, upper planar surface 126 and 128 provide an ideal surface for applying indicia or markings relevant to a medical device captured by tag 100.

As shown in FIG. 1, upper planar surface 126 and 128 contain indicia 134 and 136. Indicia 134 and 136 represent markings or tracking devices capable of retaining identifying information, for example, relevant to the medical device captured by tag 100. Additionally, indicia 134 and 136 may represent identifying information related to the patient receiving the device, medical procedure used with the device, manufacturing information such as materials, processes, customer/supplier, and lot information of similarly manufactured devices. The identifying information is not intended to be limiting in scope by this disclosure, but instead is presented for exemplarily purposes only. Furthermore, any required manufacturing standards requiring the marking of products with certain identifying information is considered to be within the scope of identifying information capable of be represented by indicia 134 and 136. Therefore, there is no need for the medical device captured by tag 100 to have identifying information because tag 100 provides any necessary identifying information.

In the present embodiment, indicia 134 and 136 represent a two dimensional bar code and alphanumeric lettering, respectively used to identify a medical device captured by tag 100. However, indicia 134 and 136, or any tracking device herein, may be any device that is capable of retaining identifying information. For example, the indicia can be a one or two dimensional barcode capable of being scanned by an optical scanner. Such an optical scanner may include a barcode scanner made by Baracoda such as the Evolution scanner (part number: B40160202).

Additionally, the tracking device or indicia may be in the form of a radio frequency identification (RFID) device built into the lobes of tag 100. Such an RFID device can transmit a radio frequency signal to an RFID transceiver that can obtain the identifying information of the medical device stored in the RFID device. Additionally, the indicia can include, for example, human readable information and/or data that may include visual alphanumeric characters and tactile features such as different surface textures and/or raised or lowered portions. Furthermore, the lobes 122 and 124 can include a sealable groove, slot, or compartment (not shown) that has a transparent cover such that any human and/or computer readable information can be placed into the sealable groove, slot, or compartment, but can still be read through upper planar surfaces 126 and 128. In addition, the indicia may include a printed adhesive label in either human and/or computer readable form that is resistant to degradation during sterilization procedures.

Furthermore, although indicia 134 and 136 are shown as two separate types of tracking devices, the identifying information contained within these indicia may contain the same amount of identifying information. However, it is also possible that one indicia may provide more identifying information than the other indicia. Additionally, there may be only one indicia on either lobe 122 or lobe 124, but not the other lobe. Furthermore, the same type of indicia may be represented on both lobes 122 and 124. Even more, lobes 122 and 124 may have only one indicia that spans consecutively across both upper planar surfaces 126 and 128.

Lobes 122 and 124 further contain a tamper evident locking mechanism that locks the first component 102 to the second component 104. In that regard, lobe 122 has a finger-like projection 138 located on the most proximal portion of tag 100. Projection 138 has a frangible connection to lobe 122. The frangible connection is created by a groove 140 extending along the width W of projection 138 at its connection with lobe 122. The thickness of projection 138 is approximately 50% less thick at its connection with lobe 122 because of groove 140. Thus, groove 140 enables the frangible connection of projection 138 to lobe 122.

Projection 138 further includes an upper surface 142 and an opposing lower surface 144. Upper surface 142 faces the same direction as upper planar surface 126, but is not coplanar. Lower surface 144 faces the same direction and is coplanar with lower planar surface 130. A raised bonding material 146 is disposed on upper surface 142. For example, the bonding material 146 may include, but is not limited to an adhesive material or unitary material formed as an energy director used in ultrasonic welding.

Lobe 124 has a corresponding recess 148 formed in the lower planar surface 132 to receive projection 138. In that manner, as shown in FIG. 2, lobes 122 and 124 are locked together by bonding projection 138 within recess 148 of lower surface 132 through the use of bonding. Bonding of projection 138 within recess 148 of lower surface 132 may be accomplished though the bonding material 146 such that an adhesive or ultrasonic welding technique bonds the projection 138 within the recess 148. Therefore, by locking lobes 122 and 124 together the first and second components 102 and 104 are locked together as well.

As stated above, the locking mechanism used between the lobes 122 and 124 is a tamper evident locking mechanism. In other words, once components 102 and 104 are locked together, then the unlocking of the components is detectable. That is the tamper evident locking mechanism is a one time use locking mechanism that is destroyed upon components 102 and 104 being unlocked from one another. In that regard, components 102 and 104 are designed to provide a clean break from one another through the frangible connection created by groove 140 extending along the width W of projection 138 at its connection with lobe 122. Components 102 and 104 are unlocked from one another by twisting, rotating, pulling, or otherwise creating stress between the components at the frangible connection created by groove 140. For example, a force may be applied to lobe 124 in the direction of arrow A1 and an opposing force applied to lobe 122 in the direction of arrow A2 to shear projection 138 at groove 140.

It should be noted that tag 100 is designed such that the frangible connection created by groove 140 has a lower resistance to stress fracturing than any other portion of tag 100. As part of this design, FIG. 2 shows a slot 150 adjacent hinge 106 that remains between the first and second components 102, 104 when these components are locked together. Slot 150 acts as a stress relief structure such that when a user applies a force to break the tamper evident closure mechanism, the mechanism makes a clean break along groove 140 before any other portion of tag 100, including hinge 106, breaks.

Furthermore, leverage nub 152 extending from lower planar surface 130 provides a leverage point for use by a healthcare provider when unlocking components 102 and 104. In fact, leverage nub 150 provides positive tactile feedback for a healthcare provider who may be wearing relative thick surgical gloves. Although not shown, there can be additional leverage nubs extending from either planar surface 130 and/or 132. Additionally, it is contemplated that any tag disclosed herein can have a surface texture that helps with gripping and/or leveraging of the tag in order to unlock the first and second components.

After unlocking components 102 and 104 from one another, the tamper evident locking mechanism cannot be used again. In that regard, the unlocking of components 102 and 104 from one another causes projection 138 to remain bonded within recess 148 and groove 140 ensures that there are no remnants of projection 138 on lobe 122. Therefore, evidence that components 102 and 104 cannot be locked together indicates tampering with tag 100 and/or the medical device captured by the tag.

Accordingly, tag 100 can be attached to and removed from a medical device with no component of tag 100 remaining permanently attached to the medical device. Furthermore, because projection 138 remains bonded within recess 148 there are no loose portions or particulates of tag 100 that separate from the tag upon unlocking the tamper evident locking mechanism. Therefore, the tamper evident locking mechanism allows tag 100 to be attached to a medical device as a one-piece tag and be separated from the medical device as a one-piece tag.

The tags disclosed herein are only temporarily attached to the medical device and are utilized for tracking the use of and associated inventory levels of the medical devices. In that regard, prior to use of a medical device having such a tag, the tag is inspected for detectable evidence of the tamper evident locking mechanism being broken and/or the tag being removed from the medical device. If there are no signs of the tag being removed from the implant and/or the tamper evident locking mechanism being broken, then a healthcare provider can remove the tag from the implant by breaking the tamper evident locking mechanism thereby releasing the medical device from the tag. If there are signs that the tamper evident locking mechanism has been tampered with and/or other evidence that the tag may have been removed from the medical device then the healthcare provider may elect not to use the medical device.

As discussed above, prior to use of the medical device the tags are capable of having indicia readable by a computer. The computer readable indicia, such as a two dimensional barcode can be scanned to create a label containing the identifying information relating to the medical device captured by the tag. In the event that a tag cannot be scanned, the human readable indicia on the tag is utilized to create the label. Subsequently, the label is attached to a patient's medical chart. Thereafter, the tag is discarded after the corresponding label has printed. In this manner the tags disclosed herein are utilized to track implant use and associated inventory levels.

Figure 3:
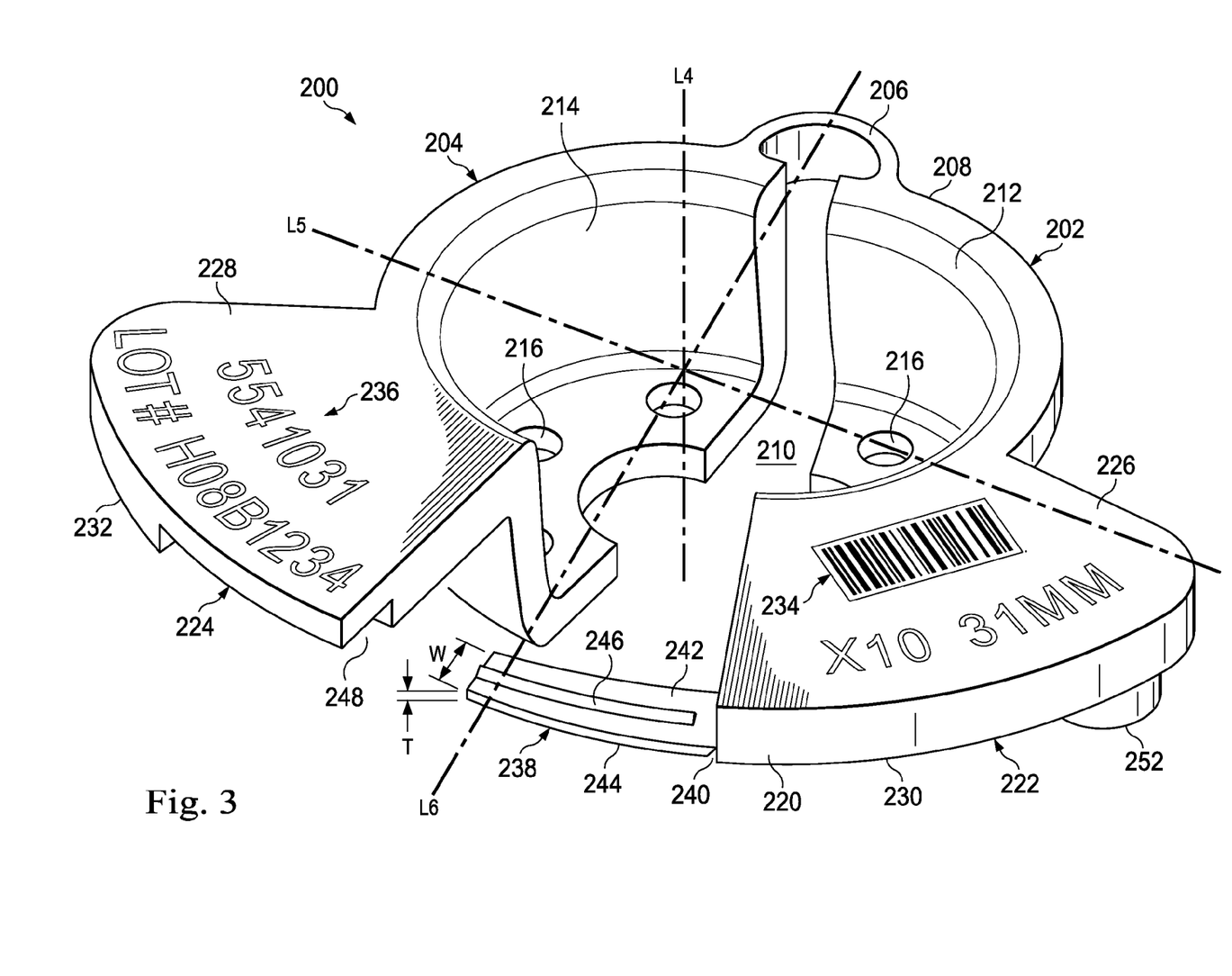
FIG. 3 is a perspective view of a tag for attachment to a medical device according to another exemplary embodiment of the present disclosure.

Referring to FIG. 3, a perspective view of a tag 200 for attachment to a medical device is shown. Tag 200 is shown in an open or unlocked position ready to capture a medical device. Tag 200 has a first component 202 and a second component 204. A hinge or web 206 flexibly connects the first component 202 and the second component 204 to each other at a distal portion 208 of tag 200. Web 206 provides sufficient flexibility to allow first and second components to move relative to each other along axes L4 (y-axis), L5 (x-axis), L6 (z-axis) and any intervening axis. In that regard, web 206 allows the first component 202 and the second component 204 to remain attached to one another while the first and second components are positioned to capture a medical device therebetween.

Additionally, the distal portion of tag 200 defines an implant or medical device receiving cavity 210. In particular, portions 212 and 214 of first and second components 202, 204, respectively, define the implant receiving cavity 210. As shown in FIG. 3, cavity 210 has a semi-circular shape to receive a medical device with the corresponding shape. However, it is contemplated that cavity 210 can be any shape in order to accommodate the medical device. For example, implant receiving cavity 210 can be circular, square, rectangular, trapezoidal, oblong, cylindrical, triangular, and any other shape necessary to receive the medical device within the cavity 210.

Furthermore, implant receiving cavity 210 is designed to allow at least a portion of a medical device to extend through cavity 210. In this manner, that tag 200 can be attached to a medical device at a plurality of locations. Additionally, it is contemplated that a portion of the medical device may extend from above and/or below cavity 210 while tag 200 is attached to the device.

Implant receiving cavity 200 further includes sterilization apertures 216. In that regard, tag 200 or any other tag disclosed herein can be attached to a medical device undergoing sterilization. Sterilization apertures 216 allow any fluid (e.g. gas or liquid) used during a sterilization process to drain from tag 200. In this manner, condensation and or other particulates present during sterilization are removed from tag 200 through sterilization apertures 216. Although, sterilization apertures 216 are shown within the base portion of portions 212 and 214, apertures 216 can be located throughout any portion of tag 200.

Tag 200 further comprises a pair of lobes 222 and 224 that extend from implant receiving cavity 210 toward a proximal portion 220 of tag 200. As shown in FIG. 2, lobes 222 and 224 extend substantially transverse from axis L4. However, lobes 222 and 224 can extend at any angle with respect to axis L4.

Lobes 222 and 224 have upper planar surfaces 226 and 228 and opposing lower surfaces 230 and 232, respectively. Upper planar surfaces 226 and 228 provide a relatively large planar surface with respect to any portion of a medical device capture by tag 200. In that manner, upper planar surfaces 226 and 228 provide an ideal surface for applying indicia or markings relevant to a medical device captured by tag 200.

As shown in FIG. 3, upper planar surface 226 and 228 contain indicia 234 and 236. Indicia 234 and 236 represent tracking devices capable of retaining identifying information, for example, relevant to the medical device captured by tag 200. Additionally, indicia 234 and 236 may represent identifying information related to the patient receiving the device, medical procedure used with the device, manufacturing information such as materials, processes, customer/supplier, and lot information of similarly manufactured devices. The identifying information is not intended to be limiting in scope by this disclosure, but instead is presented for exemplarily purposes only. Furthermore, any required manufacturing standards implanted requiring the marking of products with certain identifying information is considered to be within the scope of identifying information capable of be represented by indicia 234 and 236. Therefore, there is no need for the medical device captured by tag 200 to have identifying information because tag 200 provides any necessary identifying information.

In the present embodiment, indicia 234 and 236 represent a two dimensional bar code and alphanumeric lettering, respectively used to identify a medical device capture by tag 200. However, indicia 234 and 236, or any tracking device herein, may be any device that is capable of retaining identifying information. For example, the indicia can be a one or two dimensional barcode capable of being scanned by an optical scanner. Such an optical scanner may include a barcode scanner made by Baracoda such as the Evolution scanner (part number: B40160202).

Additionally, the tracking device or indicia may be in the form of a radio frequency identification (RFID) device built into the lobes of tag 200. Such a RFID device can transmit a radio frequency signal to an RFID transceiver that can obtain the identifying information of the medical device stored in the RFID device. Additionally, the indicia includes, for example, human readable information and/or data that may include visual alphanumeric characters and tactile features such as different surface textures and/or raised or lowered portions. Furthermore, the lobes 222 and 224 can include a sealable groove, slot, or compartment that has a transparent cover such that any human and/or computer readable information can be placed into the sealable groove, slot, or compartment, but can still be read through upper planar surfaces 226 and 228. In addition, the indicia may include a printed adhesive label in either human and/or computer readable form that is resistant to sterilization procedures.

Although indicia 234 and 236 are shown as two separate types of tracking devices, the identifying information contained within these indicia may contain the same amount of identifying information. However, it is also possible that one indicia may provide more identifying information than the other indicia. Additionally, there may be only one indicia on either lobe 222 or lobe 224, but not the other lobe. Likewise, the same type of indicia may be represented on both lobes 222 and 224. Even more, lobes 222 and 224 may have only one indicia that spans consecutively across both upper planar surfaces 226 and 228.

Lobes 222 and 224 further contain a tamper evident locking mechanism that locks the first component 202 to the second component 204. In that regard, lobe 222 has a finger-like projection 238 located on the most proximal portion of tag 200. Projection 238 has a frangible connection to lobe 222. The frangible connection is created by a groove 240 extending along the width W of projection 238 at its connection with lobe 222. The thickness of projection 238 is approximately 50% less thick at its connection with lobe 222 because of groove 240. Thus, groove 240 enables the frangible connection of projection 238 to lobe 222.

Projection 238 further includes an upper surface 242 and an opposing lower surface 244. Upper surface 242 faces the same direction as upper planar surface 226, but is not coplanar with upper planar surface 226. Lower surface 244 faces the same direction and is coplanar with lower planar surface 230. A raised bonding material 246 is disposed on upper surface 242.

As stated above, the locking mechanism used between the lobes 222 and 224 is a tamper evident locking mechanism. In other words, once components 202 and 204 are locked together, then the unlocking of the components is detectable. That is the tamper evident locking mechanism is a one time use locking mechanism that is destroyed upon components 202 and 204 being unlocked from one another. In that regard, components 202 and 204 are designed to provide a clean break from one another through the frangible connection created by groove 240 extending along the width W of projection 238 at its connection with lobe 222. Components 202 and 204 are unlocked from one another by twisting, rotating, pulling, or otherwise creating stress between the components at the frangible connection created by groove 240.

It should be noted that tag 200 is designed such that the frangible connection created by groove 240 has a lower resistance to stress fracturing than any other portion of tag 200. As part of this design, a slot adjacent hinge 206 remains between the first and second components 202, 204 when these components are locked together. This slot acts as a stress relief structure such that when a user applies a force to break the tamper evident closure mechanism, the mechanism makes a clean break along groove 240 before any other portion of tag 200, including hinge 206, breaks.

Furthermore, leverage nub 252 extending from lower planar surface 230 provides a leverage point for use by a healthcare provider when unlocking components 202 and 204. In fact, leverage nub 252 provides positive tactile feedback for a healthcare provider who may be wearing relative thick surgical gloves. Although not shown, there can be additional leverage nubs extending from either planar surface 230 and/or 232. Additionally, it is contemplated that any tag disclosed herein can have a surface texture that helps with gripping and/or leveraging the tag in order to unlock the first and second components.

After unlocking components 202 and 204 from one another, the tamper evident locking mechanism cannot be used again. In that regard, the unlocking of components 202 and 204 from one another causes projection 238 to remain bonded within recess 248 and groove 240 ensures that there are no remnants of projection 238 on lobe 222. Therefore, evidence that components 202 and 204 cannot be locked together indicates tampering with tag 200 and/or the medical device captured by the tag.

Accordingly, tag 200 can be attached and removed from a medical device with no component of tag 200 remaining permanently attached to the medical device. Furthermore, because projection 238 remains bonded within recess 248 there are no loose portions or particulates of tag 200 that separate from the tag upon unlocking the tamper evident locking mechanism. Therefore, the tamper evident locking mechanism allows tag 200 to be attached to a medical device as a one-piece tag and be separated from the medical device as a one-piece tag.

Figure 4:
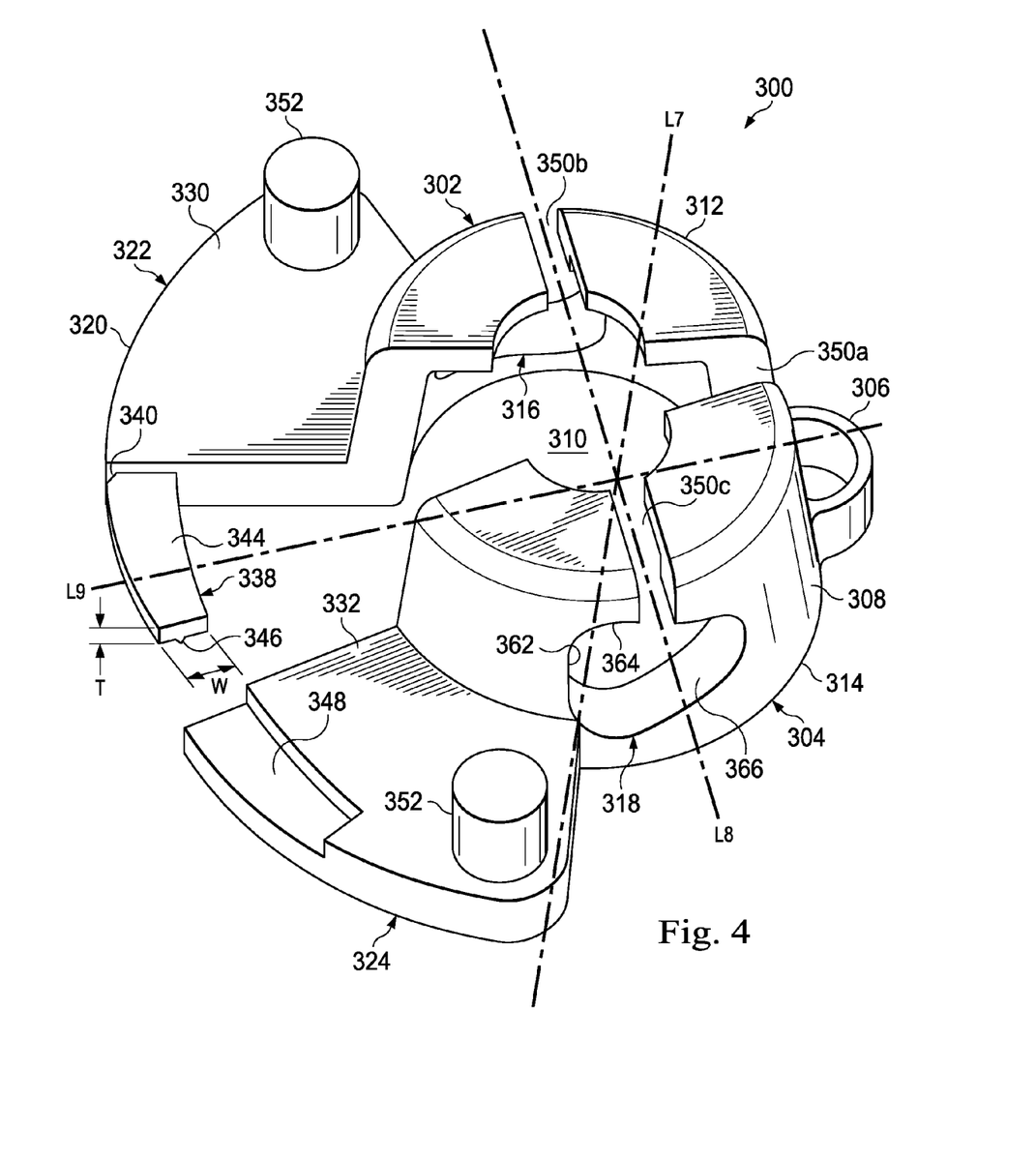
FIG. 4 is a perspective view of a tag for attachment to a medical device according to another exemplary embodiment of the present disclosure.
Figure 7:
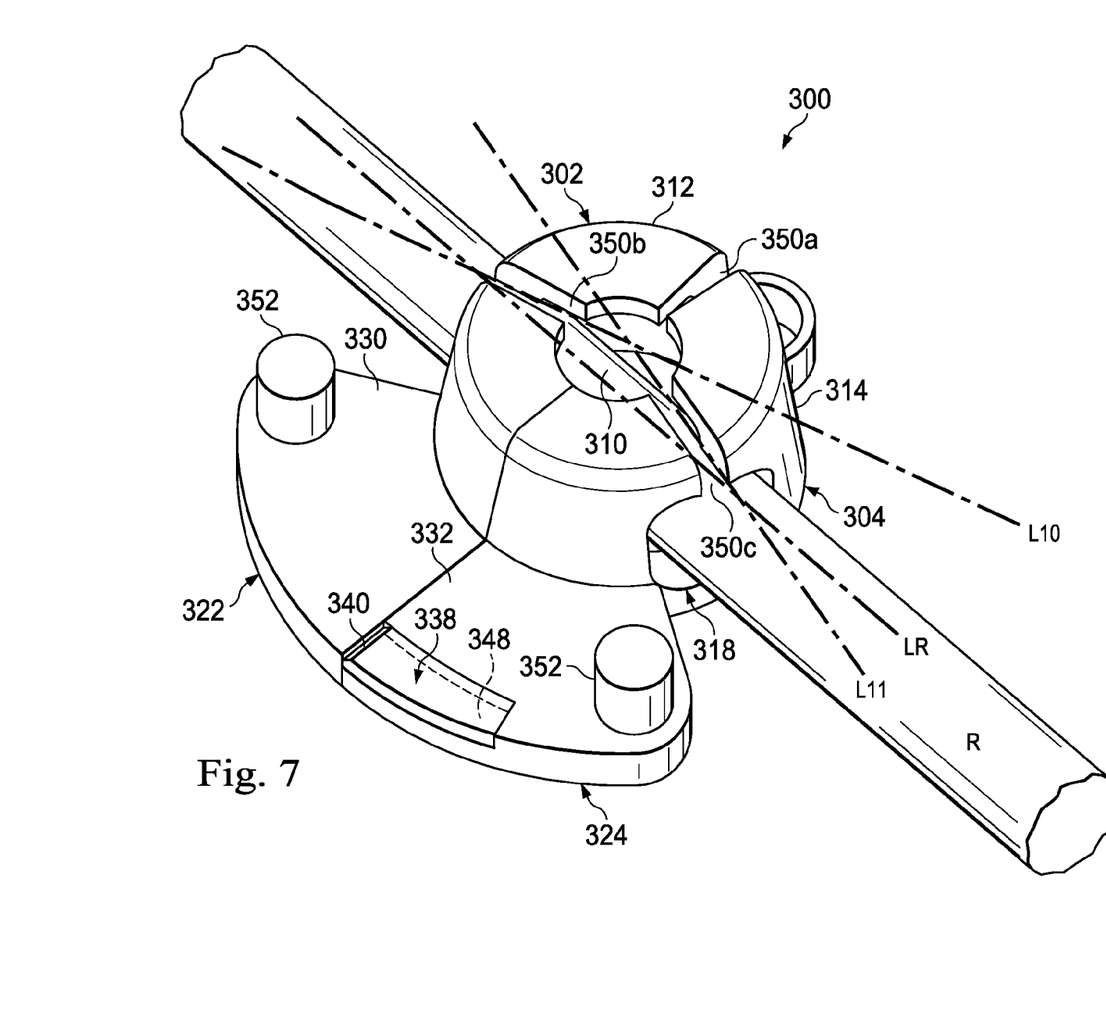
FIG. 7 is a perspective view of the tag of FIG. 4 locked onto a spinal rod.

Referring to FIG. 4, a perspective view of a tag 300 for attachment to a medical device is shown. Tag 300 is shown in an open or unlocked position ready to capture a medical device. Tag 300 has a first component 302 and second component 304. A hinge or web 306 flexibly connects the first component 302 and second component 304 to each other at a distal portion 308 of tag 300. Web 306 provides sufficient flexibility to allow the first and second components to move relative to each other along axes L7 (y-axis), L8 (x-axis), L9 (z-axis), and any intervening axis. In that regard, web 306 allows the first component 302 and second component 304 to remain attached to one another while the hinge is disposed in the open position of FIG. 4 and as it is positioned in a closed position to capture a medical device therebetween as shown in FIG. 7.

Additionally, the distal portion of tag 300 defines an implant or medical device receiving cavity 310. In particular, portions 312 and 314 of the first and second components 302, 304 define the implant receiving cavity 310. As shown in FIG. 4, cavity 310 has a semi-circular shape (as viewed along axis L7) to receive a medical device with the corresponding shape. However, it is contemplated that cavity 310 can be any shape in order to accommodate the medical device. For example, implant receiving cavity 310 can be circular, semi-circular, square, rectangular, trapezoidal, oblong, cylindrical, triangular, and any other shape necessary to receive the medical device within the cavity 310.

Figure 5:
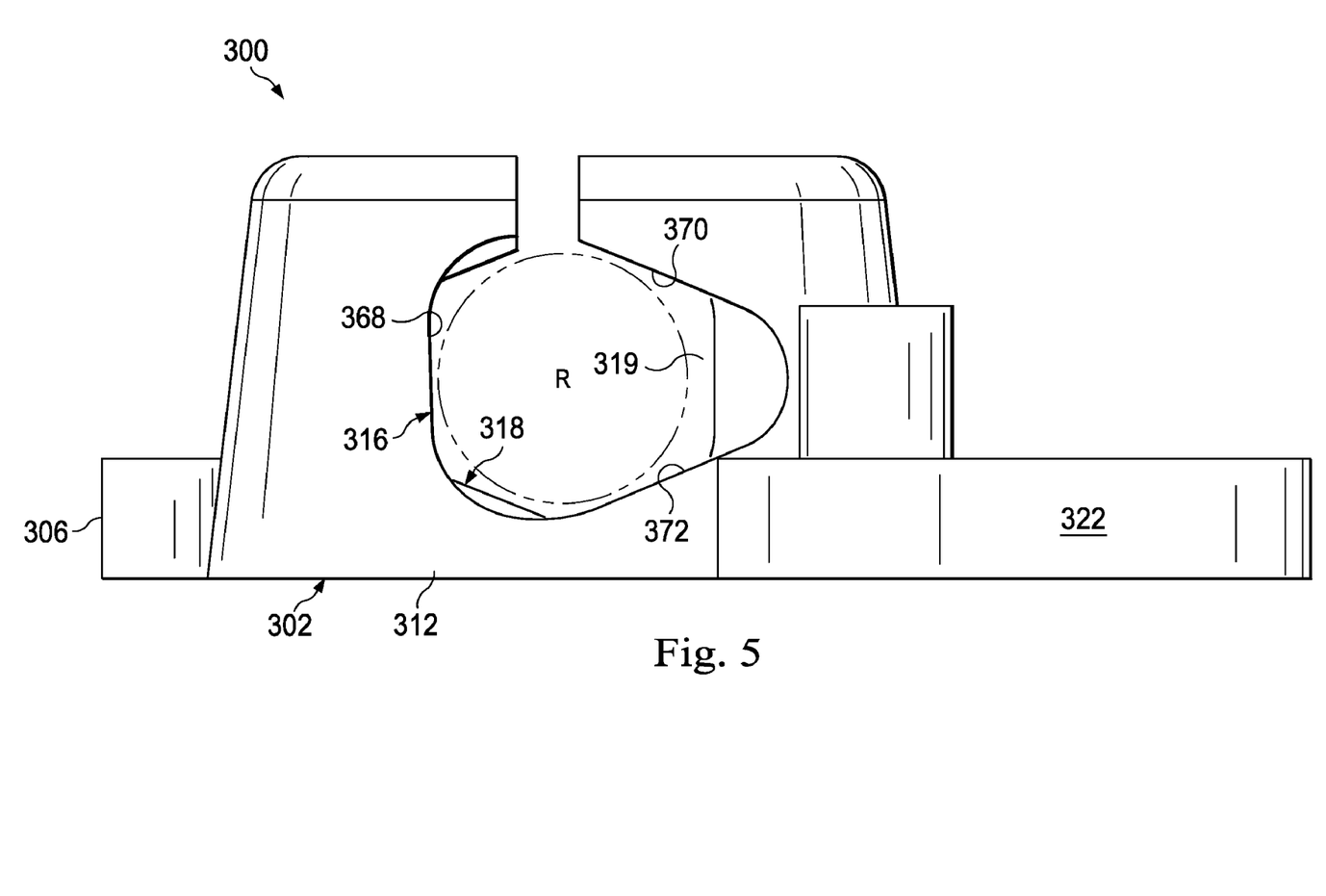
FIG. 5 is a side view of the tag of FIG. 4 where the tag is in an unlocked position.

Furthermore, portions 312 and 314 forming implant receiving cavity 310 each have an implant receiving aperture 316 and 318, respectively. Apertures 316 and 318 are designed to receive a medical device. In that manner, apertures 316 and 318 facilitate receiving a medical device having an elongated member capable of extending through these apertures into implant receiving cavity 310. For example, FIG. 5 shows a side view of tag 300 in the open position with a medical device, such as spinal rod R, extending through implant receiving aperture 316 into implant receiving cavity 310.

As shown in FIG. 4, implant receiving apertures 316, 318 are aligned with one another relative to longitudinal axis L8 or a midline of the implant receiving cavity 310. The implant receiving apertures 316 and 318 are generally triangular in shape. In that regard, portion 314 has a base bearing surface 362 and an upper bearing surface 364 opposing a lower bearing surface 366 tapering towards one another to a closed or pointed end to form aperture 318. Likewise, as shown in FIG. 5, portion 312 also has a base bearing surface 368 as well as an upper bearing surface 370 and opposing lower bearing surface 372 tapering towards one another to a closed or pointed end to form aperture 316. As discussed in more detail below, these bearing surfaces act as a three point locking mechanism such that a medical device captured by tag 300 in a closed position is friction fitted to the tag via these three points of contact.

Implant receiving apertures 316 and 318 are non-mirror images of each other. In fact, the closed or pointed ends of the triangular shaped apertures 316 and 318 generally point opposing directions relative to each other along longitudinal axis L9. Although apertures 316 and 318 are generally described above as triangular in shape, it is contemplated that apertures 316 and 318 can be any shape in order to accommodate the medical device. For example, implant receiving apertures 316 and 318 can be circular, semi-circular, square, rectangular, trapezoidal, oblong, cylindrical, and any other shape necessary to receive the medical device through implant receiving apertures 316 and 318.

As discussed above, FIG. 5 shows a side view of tag 300 in the open position. Implant receiving apertures are generally aligned along axis L8 to define an implant receiving channel 319 shown in FIG. 5. Spinal rod R is positioned through implant receiving aperture 316 into implant receiving cavity 310. In the open configuration the implant receiving channel 319 is unobstructed such that spinal rod R is capable of being positioned through aperture 316 into cavity 310 and extend out of aperture 318. In other words, the base bearing surface 368 as well as an upper bearing surface 370 and opposing lower bearing surface 372 that form aperture 316 do not prohibit spinal rod R from being positioned within cavity 310. In that regard, spinal rod R is rotatable and slidable while extending through apertures 316 and 318 into cavity 310 when tag 300 is in the open position. Therefore, tag 300 can be positioned relative to spinal rod R at a plurality of locations along a longitudinal axis of spinal rod R.

Figure 6:
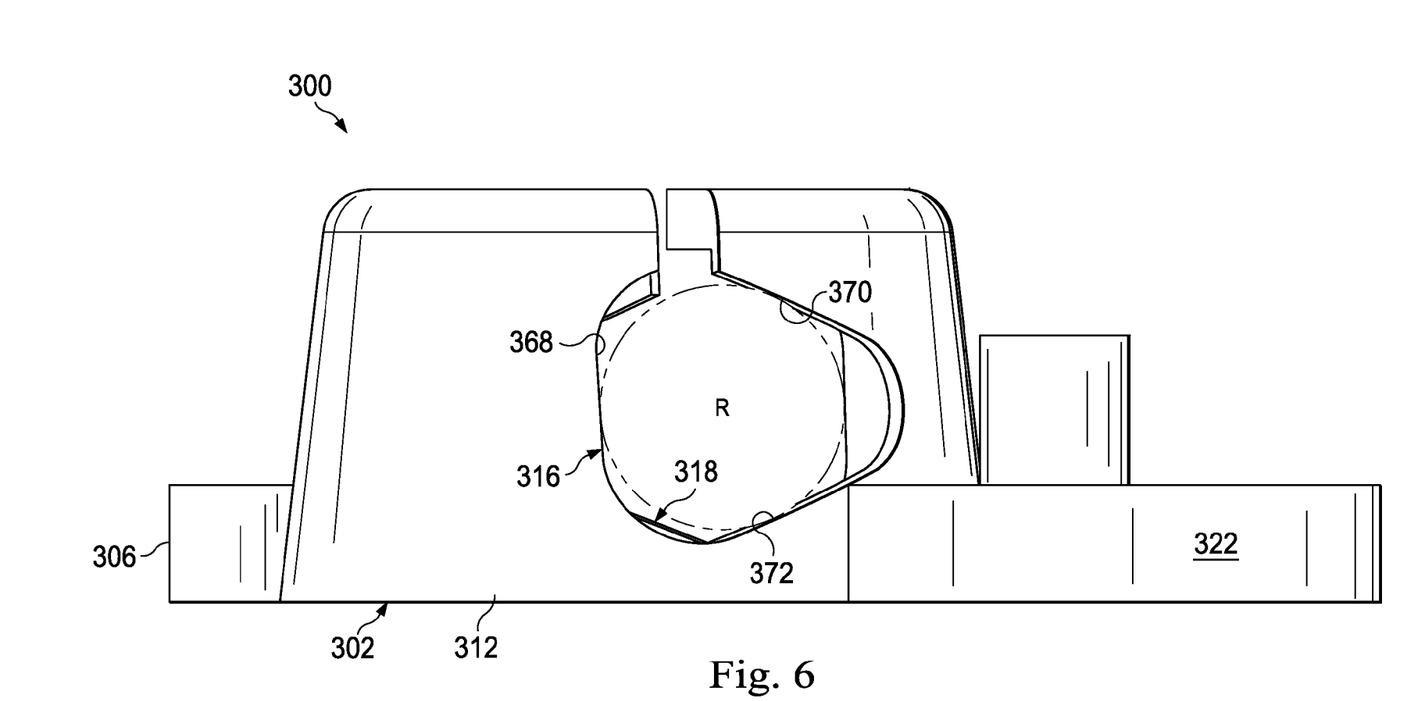
FIG. 6 is another side view of the tag of FIG. 4 where the tag is in a locked position.

FIG. 6 shows a side view of tag 300 in a closed or locked position. As discussed in greater detail below, components 302 and 304 can be locked together thereby locking portions 312 and 314 together. In locking portions 312 and 314 together, base bearing surfaces 362 and 368 of portions 312 and 314, respectively are moved towards one another along longitudinal axis L9 to close the implant receiving channel 319 about the rod R. In this manner, base bearing surfaces 362 and 368 apply opposing forces relative to one another along longitudinal axis L9 against spinal rod R positioned through apertures 316 and 318. Specifically, base bearing surfaces 362 and 368 exert opposing forces on spinal rod R causing the rod to move along upper bearing surfaces 364, 370 and lower bearing surfaces 366, 372 in the relative direction that the triangular shaped apertures 316 and 318 generally point along longitudinal axis L9. Thus, the bearing surfaces of portions 312 and 314 exert forces on spinal rod R thereby securing tag 300 to the rod by a friction fit against the bearing surfaces of apertures 316 and 318. Therefore, spinal rod R is captured by tag 300 via a three point contact locking mechanism comprised of the base bearing surfaces and opposing upper and lower bearing surfaces of portions 312 and 314, respectively.

It should be noted that the base bearing surfaces and opposing upper and lower bearing surfaces of portions 312 and 314, respectively in some embodiments can be deformable. In such an embodiment, when spinal rod R is captured by tag 300 via the three point contact locking mechanism described above, those portions of base bearing surfaces and opposing upper and lower bearing surfaces of portions 312 and 314 in contact with spinal rod R may deform to the shape of spinal rod R. Thus, spinal rod R may be further captured by tag 300 via the deformation of those portions of base bearing surfaces and opposing upper and lower bearing surfaces of portions 312 and 314 in contact with spinal rod R.

Referring again to FIG. 4, Tag 300 further comprises a pair of lobes 322 and 324 that extend from implant receiving cavity 310 toward a proximal portion 320 of tag 300. Lobes 322 and 324 extend substantially transverse from axis L7 or, as shown in FIG. 7, substantially parallel from a longitudinal axis LR of spinal rod R. However, lobes 322 and 324 can extend at any angle with respect to axis L7 or LR.

Lobes 322 and 324 have upper planar surfaces (not shown) and opposing lower surfaces 330 and 332, respectively. Upper planar surfaces provide a relatively large planar surface with respect to any portion of a medical device capture by tag 300. In that manner, upper planar surfaces provide an ideal surface for applying indicia or markings relevant to a medical device captured by tag 300.

Similarly to upper planar surface 126 and 128 shown in FIG. 1, upper planar surfaces of tag 300 can contain indicia. Indicia represent tracking devices capable of retaining identifying information, for example, relevant to the medical device captured by tag 300. Additionally, indicia may represent identifying information related to the patient receiving the device, medical procedure used with the device, manufacturing information such as materials, processes, customer/supplier, and lot information of similarly manufactured devices. The identifying information is not intended to be limiting in scope by this disclosure, but instead is presented for exemplarily purposes only. Furthermore, any required manufacturing standards implanted requiring the marking of products with certain identifying information is considered to be within the scope of identifying information capable of be represented by indicia. Therefore, there is no need for the medical device captured by tag 300 to have identifying information because tag 300 provides any necessary identifying information.

Any indicia or tracking device used herein with tag 300, may be any device that is capable of retaining identifying information. For example, the indicia can be a one or two dimensional barcode capable of being scanned by an optical scanner. Such an optical scanner may include a barcode scanner made by Baracoda such as the Evolution scanner (part number: B40160202).

Additionally, the tracking device or indicia may be in the form of a radio frequency identification (RFID) device built into the lobes of tag 300. Such a RFID device can transmit a radio frequency signal to an RFID transceiver that can obtain the identifying information of the medical device stored in the RFID device. Additionally, the indicia includes, for example, human readable information and/or data that may include visual alphanumeric characters and tactile features such as different surface textures and/or raised or lowered portions. Furthermore, the lobes 322 and 324 can include a sealable groove, slot, or compartment that has a transparent cover such that any human and/or computer readable information can be placed into the sealable groove, slot, or compartment, but can still be viewed through the upper planar surfaces of tag 300. In addition, the indicia may include a printed adhesive label in either human and/or computer readable form that is resistant to sterilization procedures.

Furthermore, it is contemplated that the indicia associated with tag 300 may be two or more separate indicia located respectively on the upper planar surface of lobes 322 and 324. The identifying information contained within these separate indicia may contain the same amount of identifying information. However, it is also possible that one indicia may provide more identifying information than the other indicia. Additionally, there may be only one indicia on either lobe 322 or lobe 324, but not on the other lobe. Likewise, the same type of indicia may be represented on both lobes 322 and 324. Even more, lobes 322 and 324 may have only one indicia that spans consecutively across both upper planar surfaces of lobes 322 and 324.

Lobes 322 and 324 further contain a tamper evident locking mechanism that locks the first component 302 to the second component 304. In that regard, lobe 322 has a finger-like projection 338 located on the most proximal portion of tag 300. Projection 338 has a frangible connection to lobe 322. The frangible connection is created by a groove 340 extending along the width W of projection 338 at its connection with lobe 322. The thickness of projection 338 is approximately 50% less thick at its connection with lobe 322 because of groove 340. Thus, groove 340 enables the frangible connection of projection 338 to lobe 322.

Projection 338 further includes an upper surface (not shown) and an opposing lower surface 344. The upper surface of projection 338 faces the same direction as the upper planar surface of lobe 322, but is not coplanar with the upper planar surface of lobe 322. Lower surface 344 faces the same direction and is coplanar with lower planar surface 330. A raised bonding material 346 is disposed on the upper surface of projection 338.

Lobe 324 has a corresponding recess 348 formed in the lower planar surface 332 to receive projection 338. In that manner, as shown in FIG. 7, lobes 322 and 324 are locked together by bonding projection 338 within recess 348 of lower surface 332 through the use of bonding material 346. Bonding of projection 338 within recess 348 of lower surface 332 may be accomplished though bonding with an adhesive or ultrasonic welding technique bonds the projection 338 within the recess 348. Therefore, by locking lobes 322 and 324 together the first and second components 302 and 304 are locked together as well.

As stated above, the locking mechanism used between the lobes 322 and 324 is a tamper evident locking mechanism. In other words, once components 302 and 304 are locked together then the unlocking of the components is detectable. That is the tamper evident locking mechanism is a one time use locking mechanism that is destroyed upon components 302 and 304 being unlocked from one another. In that regard, components 302 and 304 are designed to provide a clean break from one another through the frangible connection created by groove 340 extending along the width W of projection 338 at its connection with lobe 322. Components 302 and 304 are unlocked from one another by twisting, rotating, pulling, or otherwise creating stress between the components at the frangible connection created by groove 340.

It should be noted that tag 300 is designed such that the frangible connection created by groove 340 has a lower resistance to stress fracturing than any other portion of tag 300. As part of this design, FIG. 4 shows that portions 312 and 314 are configured to have a slot 350a formed between these portions that is adjacent hinge 306. While tag 300 is in the unlocked or open position, slot 350a is in an unflexed or relaxed condition extending substantially parallel to longitudinal axis L9 and substantially transverse to longitudinal axis L8. Furthermore, FIG. 4 shows that portion 312 has a slot 350b that extends into implant receiving aperture 316 and that portion 314 has a slot 350c that extends into implant receiving aperture 318. As shown, slots 350b and 350c are in an unflexed or relaxed condition. Additionally, slots 305b and 350c are aligned with one another and extend substantially parallel to longitudinal axis L8 and substantially transverse to longitudinal axis L9 while tag 300 is in the unlocked position.

Slots 350a-c provide tag 300 with some flexibility between and within component 302 and 304 when the tag 300 is locked around a medical device. In that regard, as shown in FIG. 7, slot 350a is in a flexed or stressed condition, such that the width of slot 350a is narrowed between the first and second components 302, 304 when these components are locked together. Additionally, slots 350b-c are also shown in a flexed or stressed condition such that the width of these slots may narrow when tag 300 is locked or closed position. As shown in FIGS. 4 and 5, slots 350b and 350c extend along axis L8 in the relaxed condition. However, slots 350b and 350c extend along longitudinal axes L10 and L11 at oblique angles with respect to the longitudinal axis LR of spinal rod R when the first and second components 302, 304 are locked together. Thus, because slots 350a-c allow flexibility between components 302 and 304 these slots act as stress relief structures such that components 302 and 304 break apart along a designed fracture plane (e.g. longitudinal axis L9). Therefore, when a healthcare provider applies a force to break the tamper evident closure mechanism of a locked tag 300, theses slots help ensure that the mechanism makes a clean break along groove 340 before any other portion of tag 300.

Furthermore, leverage nubs 352 extending from lower planar surfaces 330 and 332 provide leverage points for use by a healthcare provider when unlocking components 302 and 304. In fact, leverage nubs 352 provide positive tactile feedback for a healthcare provider who may be wearing relative thick surgical gloves. Although not shown, there can be additional leverage nubs extending from either planar surface 330 and/or 332. Additionally, it is contemplated that any tag discloses herein can have a surface texture that helps with gripping and/or leveraging the tag in order to unlock the first and second components.

After unlocking components 302 and 304 from one another, the tamper evident locking mechanism cannot be used again. In that regard, unlocking of components 302 and 304 from one another causes projection 338 to remain bonded within recess 348 and groove 340 ensures that there are no remnants of projection 338 on lobe 322. Therefore, evidence that components 302 and 304 cannot be locked together indicates tampering with tag 300 and/or the medical device captured by the tag.

Accordingly, tag 300 can be attached and removed from a medical device with no component of tag 300 remaining permanently attached to the medical device. Furthermore, because projection 338 remains bonded within recess 348 there are no loose portions loose portions or particulates of tag 200 that separate from the tag upon unlocking the tamper evident locking mechanism. Therefore, the tamper evident locking mechanism allows tag 300 to be attached to a medical device as a one-piece tag and be separated from the medical device as a one-piece tag.

It should be noted the tamper evident locking mechanism for locking the various first and second components discussed above may be accomplished, without limitation, by applying adhesive between the components. Additionally, the tamper evident locking mechanism for locking the various first and second components discussed above may be accomplished, without limitation, by providing a ratcheting or snap-fit connection between the components that is designed to fracture before other portions of the tag when stressed. Furthermore, the tamper evident locking mechanism for locking the various first and second components discussed above may be accomplished, without limitation, by melting, welding, ultrasonic welding or otherwise joining all or a portion of the components together.

Furthermore, the tamper evident locking mechanism for locking the various first and second components discussed above may include an indicator device across a joint between or through the components that fracture, change shape, change color, or otherwise are altered by separation of the first and second components. Detectable separation of the components may occur at one or more connections between the components, or may include facture or change within either or both of the first and second components.

The tags disclosed herein are in whole or in part may be constructed of biocompatible materials of various types including metals or polymers. For example, the tags may be made in whole or in part of a polymer known as Radel R. In such a scenario, a tag is formed in whole or in part using Radel R polymer mixed with barium sulfate ($BaSO_4$). In this manner, the tag is radiopaque such that in case of accidental implantation the tag can be located via an x-ray, for example. Further, examples of tag materials include, but are not limited to, non-cobalt-chromium alloys, titanium alloys, nickel titanium alloys, and/or stainless steel alloys, plastics and polymers including without limitation any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE.

Although the tags described herein are used to track and trace a bone screw (FIG. 2) and spinal rod (FIG. 7) this is no way implies a limitation of such medical devices the tags can be associated with and used to track. The medical device capable of being tracked by the tags described herein may be any implant or instrument used in accomplish a medical procedure. In that regard, the medical device of some embodiments may be, without limitation, a surgical screw of any variety, a spinal or other orthopedic plate, a surgical rod, an interbody spinal device, a vertebral disc arthroplasty device, a nucleus replacement device, a corpectomy device, a vertebrectomy device, a mesh device, a facet fixation or arthroplasty device, a structural bone graft, a staple, a tether of synthetic material or wire, or other spinal fixation instrumentation, an intramedullary nail, an external fixation device, a hip prosthesis or therapeutic device, a knee prosthesis or therapeutic device, or an instrument useful with any of the previously recited devices.

The tags and indicia and medical devices described herein are capable of undergoing one or more steam sterilization cycles, or other sterilization procedures such as radiation or gas sterilization, without degrading in a manner that would make the tag unusable and the implant unsuitable for use in a medical procedure. Therefore, the medical devices can be shipped non-sterilized from the manufacture to a healthcare provider, but the non-sterile medical device can still be tracked for inventory purposes and uses thereof through the use of the tags described herein.

The medical device of this or any other embodiment of the invention may consist of materials, by way of example, and without limitation, including titanium and its alloys, ASTM material, cobalt chrome, tantalum, ceramic, poly-ether-ether-ketone (PEEK), PEAK, various plastics, plastic composites, carbon fiber composites, coral, allograft, autograft, zenograft, and can include artificial materials which are at least in part bioresorbable, or any material suitable for human implantation.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept. It is understood that all spatial references, such as "longitudinal axis," "horizontal," "vertical," "top," "upper," "lower," "bottom," "left," and "right," are for illustrative purposes only and can be varied within the scope of the disclosure.

What is claimed is:

1. A tag for tracking inventory levels and uses of an implant, the tag comprising:
    a first component having a proximal portion and a distal portion;
    a second component having a proximal portion and distal portion,
    an implant receiving cavity formed by the distal portion of the first component and the distal portion of the second component,
    a planar surface formed by the proximal portion of the first component and the proximal portion of the second component, the planar surface extending from the implant receiving cavity such that the planar surface is substantially transverse to a longitudinal axis of the implant received within the implant receiving cavity, the planar surface including indicia; and
    a tamper evident locking mechanism configured for locking the first component to the second component, the tamper evident locking mechanism providing an unlocked position for receiving an implant between the first and second components within the implant receiving cavity and a locked position in which the first and second components are locked together preventing the implant from being released from the cavity without detectable evidence,
    wherein at least a portion of the first and second components is radiopaque.

2. The tag of claim 1, wherein the first and second components further include a plurality of projections extending into the implant receiving cavity to engage a corresponding recess of the implant received within the cavity thereby locking the rotational alignment of the tag with respect to the implant.

3. The tag of claim 1, wherein the tag comprises a material capable of undergoing sterilization without degradation such that the indicia remains readable after sterilization of the tag, the indicia includes at least one of a human readable and computer readable form.

4. The tag of claim 1, wherein the indicia provides identifying information relating to at least one of the implant, a patient receiving the implant, a medical procedure used with the implant, and a material and process of manufacturing associated with the implant.

5. The tag of claim 1, wherein the distal portion of the first component further includes at least one stress relief structure, the at least one stress relief structure ensures that the first and second components separate along a fracture plane that is substantially transverse to a midline of the implant receiving cavity and includes a portion of the tamper evident locking mechanism.

6. The tag of claim 1, wherein at least a portion of the first and second components forming the implant receiving cavity includes a plurality of apertures allowing particulate to drain away from the cavity and the implant received within the cavity while the implant with the tag coupled thereto undergo sterilization.

7. A tag for tracking inventory levels and uses of an implant, the tag comprising:
    a first component with a first lobe and a second component with a second lobe forming an implant receiving cavity;
    the first lobe and the second lobe extending substantially perpendicular from a longitudinal axis of the implant received within the implant receiving cavity, the first and second lobes forming a planar surface having indicia;
    a web flexibly connecting the first and second lobes such that the lobes are separable along a first plane that is substantially coplanar with the planar surface and along a second plane that is substantially transverse to the planar surface; and
    a tamper evident locking mechanism having an unlocked position in order for receiving an implant between the first and second components within the implant receiving cavity and a locked position in which the first and second components are locked together preventing the implant from being released from the cavity without detectable evidence.

8. The tag of claim 7, wherein the detectable evidence includes evidence that the tamper evident locking mechanism is unable to assume the locked position.

9. The tag of claim 7, wherein the tamper evident locking mechanism is associated with the at least one lobe from both the first and second components, the tamper evident locking mechanism comprising:
    a projection associated with the first lobe, the projection having a frangible connection with the first lobe from the first component; and
    a recess associated with the second lobe, the recess sized and shaped to receive the projection,
    wherein the projection is secured within the recess when the tamper evident locking mechanism is in the locked position.

10. The tag of claim 9, wherein the frangible connection enables the first lobe have a clean break from the second lobe when the tamper evident locking mechanism is in the locked position, the clean break enabling the projection to remain secured within the recess associated with the second lobe when the tamper evident locking mechanism is broken to release the implant.

11. The tag of claim 10, wherein the projection is secured within the recess via bonding of the projection to an interior of the recess.

12. The tag of claim 7, wherein the indicia provides identifying information relating to at least one of the implant, a patient receiving the implant, a medical procedure used with the implant, and a material and process of manufacturing associated with the implant.

13. A tag for tracking inventory levels and uses of an implant, the tag comprising:
    a first component and a second component forming an implant receiving cavity;
    a hinge joining the first component to the second component and moveable between an open position and a closed position;
    a first implant receiving aperture having a first longitudinal axis defined in the first component and an opposing second implant receiving aperture having a second longitudinal axis defined in the second component, the first and second implant receiving apertures sized and shaped for receiving the implant;

a stress relief structure defined on at least one of the first and second components, wherein in the open position the stress relief structure is in a relaxed condition and the first longitudinal axis is generally aligned with the second longitudinal axis and in the closed position the stress relief structure is in a flexed condition and the first longitudinal axis is generally skewed from the second longitudinal axis;

wherein the first component further comprises a first base bearing surface and a first upper bearing surface opposing a first lower bearing surface, the first upper and lower bearing surfaces extending from the first base surface and tapering towards a first distal end to form the first implant receiving aperture; and wherein the second component further comprises a second base bearing surface and a second upper bearing surface opposing a second lower bearing surface, the second upper and lower bearing surfaces extending from the second base surface and tapering towards a second distal end to form the second implant receiving aperture.

14. The tag of claim 13, wherein the stress relief structure is aligned with the first longitudinal axis.

15. The tag of claim 13, wherein the first base bearing surface exerts a first force on the implant received within the first implant receiving aperture such that the implant is forced along the first upper and lower bearing surfaces towards the first distal end, wherein the second bearing surface exerts a second force on the implant received within the second implant receiving aperture such that the implant is forced along the second upper and lower bearing surfaces towards the second distal end, wherein the first and second forces are substantially equal to one another thereby locking the rod within the first and second implant receiving apertures.

16. The tag of claim 15, wherein the first base bearing surfaces exerts the first force along a plane substantially opposing the second force exerted by the second base bearing surface.

17. The tag of claim 15, wherein the first base bearing surface exerting the first force forms a three point contact locking mechanism around the implant, the three point contact locking mechanism comprising:

a first contact point between the first base bearing surface and the implant;

a second contact point between the first upper bearing surface and the implant; and a third contact point between the first lower bearing surface and the implant.

* * * * *